(12) United States Patent
Mora Lopez

(10) Patent No.: US 10,811,542 B2
(45) Date of Patent: Oct. 20, 2020

(54) PSEUDO-RESISTOR STRUCTURE, A CLOSED-LOOP OPERATIONAL AMPLIFIER CIRCUIT AND A BIO-POTENTIAL SENSOR

(71) Applicant: IMEC VZW, Leuven (BE)

(72) Inventor: Carolina Mora Lopez, Leuven (BE)

(73) Assignee: IMEC VZW, Leuven (BE)

( * ) Notice: Subject to any disclaimer, the term of this patent is extended or adjusted under 35 U.S.C. 154(b) by 65 days.

(21) Appl. No.: 16/176,448

(22) Filed: Oct. 31, 2018

(65) Prior Publication Data

US 2019/0131462 A1    May 2, 2019

(30) Foreign Application Priority Data

Oct. 31, 2017  (EP) ..................................... 17199388

(51) Int. Cl.
*H01L 29/8605* (2006.01)
*H01L 27/07* (2006.01)
(Continued)

(52) U.S. Cl.
CPC ...... *H01L 29/8605* (2013.01); *A61B 5/04002* (2013.01); *G01N 27/045* (2013.01);
(Continued)

(58) Field of Classification Search
CPC .............. G01N 27/045; H01L 27/0788; H01L 29/0688; H01L 29/861; H01L 29/8605;
(Continued)

(56) References Cited

U.S. PATENT DOCUMENTS 8,072,269 B2 * 12/2011 Wu ........................... H03F 1/26
                                                        330/253
8,344,810 B2 *  1/2013 Lian ........................ H03F 3/187
                                                        330/305
(Continued)

FOREIGN PATENT DOCUMENTS

CN        107104641 A      8/2017
WO    WO2009151406 A1    12/2009

OTHER PUBLICATIONS

Ilku Nam et al., "Low 1/F Noise and DC Offset RR Mixer for Direct Conversion Receiver Using Parasitic Vertical NPN Bipolar Transistor in Deep N-Well CMOS Technology", Symposium on VLSI Circuits. Digest of Technical Papers, 2003.
(Continued)

*Primary Examiner* — Peniel M Gumedzoe
(74) *Attorney, Agent, or Firm* — Moser Taboada

(57) ABSTRACT

A pseudo-resistor structure, comprises: a first and a second PMOS transistor or PN diode configured as two-terminal devices, wherein the positive terminal of the first PMOS transistor or PN diode is connected to the positive terminal of the second PMOS transistor or PN diode, and wherein the negative terminal of the first PMOS transistor or PN diode is connected to an input (A) of the pseudo-resistor structure and wherein the negative terminal of the second PMOS transistor or PN diode is connected to an output (C) of the pseudo-resistor structure, and a dummy transistor or dummy diode connected to the input (A), wherein the dummy transistor or dummy diode is further connected to a bias voltage for compensating a leakage current through the first and the second PMOS transistors or PN diodes. A closed-loop operational amplifier circuit comprising the pseudo-resistor structure is provided. Also, a bio-potential sensor
(Continued)

comprising the closed-loop operational amplifier circuit is provided.

17 Claims, 5 Drawing Sheets

(51) Int. Cl.
    *H01L 29/06*     (2006.01)
    *H03F 3/45*     (2006.01)
    *H01L 29/861*     (2006.01)
    *G01N 27/04*     (2006.01)
    *A61B 5/04*     (2006.01)

(52) U.S. Cl.
    CPC ...... *H01L 27/0788* (2013.01); *H01L 29/0688* (2013.01); *H01L 29/861* (2013.01); *H03F 3/45071* (2013.01); *H03F 3/45475* (2013.01); *H03F 2200/129* (2013.01); *H03F 2200/261* (2013.01); *H03F 2200/264* (2013.01); *H03F 2200/297* (2013.01); *H03F 2200/42* (2013.01); *H03F 2203/45116* (2013.01); *H03F 2203/45151* (2013.01); *H03F 2203/45152* (2013.01); *H03F 2203/45156* (2013.01); *H03F 2203/45174* (2013.01); *H03F 2203/45224* (2013.01); *H03F 2203/45512* (2013.01); *H03F 2203/45518* (2013.01); *H03F 2203/45524* (2013.01); *H03F 2203/45526* (2013.01); *H03F 2203/45544* (2013.01); *H03F 2203/45546* (2013.01); *H03F 2203/45548* (2013.01); *H03F 2203/45594* (2013.01); *H03F 2203/45602* (2013.01); *H03F 2203/45604* (2013.01); *H03F 2203/45631* (2013.01); *H03F 2203/45632* (2013.01); *H03F 2203/45698* (2013.01); *H03F 2203/45712* (2013.01)

(58) Field of Classification Search
    CPC ............. H03F 3/45071; H03F 3/45475; A61B 5/04002
    See application file for complete search history.

(56) References Cited

U.S. PATENT DOCUMENTS

2013/0069716 A1    3/2013   Shiue et al.
2016/0338612 A1    11/2016   Nuo et al.

OTHER PUBLICATIONS

Reid R. Harrison et al., "A Low-Power Low-Noise CMOS Amplifier for Neural Recording Applications", IEEE Journal of Solid-State Circuits, vol. No. 38, Issue No. 6, pp. 958-965, Jun. 2003.
Pedro Luiz Benko et al., "Bio-Amplifier Based on MOS Bipolar Pseudo-Resistors: A New Approach Using Its Non-Linear Characteristic", Journal of Integrated Circuits and Systems, vol. 11, Issue No. 2, pp. 132-139, 2016.
European Search Report dated Apr. 25, 2018 for Application No. EP17199388.4.

\* cited by examiner

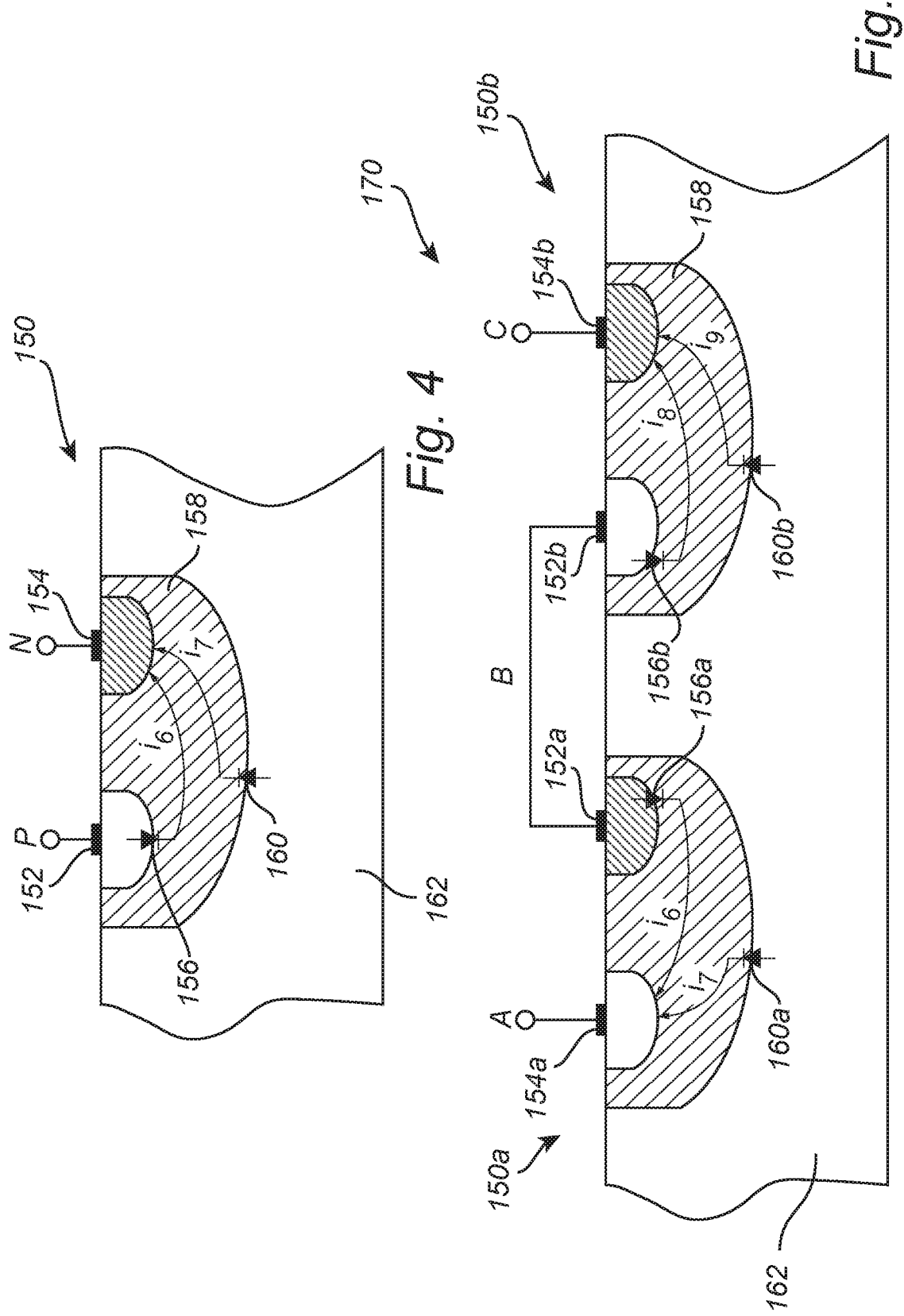

PSEUDO-RESISTOR STRUCTURE, A CLOSED-LOOP OPERATIONAL AMPLIFIER CIRCUIT AND A BIO-POTENTIAL SENSOR

CROSS-REFERENCE TO RELATED APPLICATIONS

This application claims the benefit of European Application Number 17199388.4, filed on 31 Oct. 2017, herein incorporated by reference in its entirety.

TECHNICAL FIELD

The present inventive concept relates to a pseudo-resistor structure. The present inventive concept also relates to a closed-loop operational amplifier circuit incorporating a pseudo-resistor structure and a bio-potential sensor incorporating a closed-loop operational amplifier circuit.

BACKGROUND

In applications where a low frequency signal is to be sensed, it may be difficult to eliminate or remove direct current (DC) signals, while maintaining the low frequency signal of interest. A large DC signal may severely affect sensing of the low frequency signal, so it may be of utmost importance to remove the DC signal.

In sensing of bio-signals, it may often be desired that low frequency information is acquired. The signal to be measured may typically be weak and the measuring may also be associated with large DC signals. For instance, relatively large DC offsets may originate in an interface between an electrode and bio-material. Thus, the DC offset may destroy possibilities of analyzing the low frequency information of interest, unless the DC signal is eliminated or removed.

DC offset cancellation could be implemented using large-size capacitors and/or resistors. However, in miniaturizing of devices, another approach to DC offset cancellation is needed. It is therefore known to use a pseudo-resistor, which may emulate very large resistances for DC signals such that the pseudo-resistor forms a DC blocking high-pass filter. The use of pseudo-resistors may thus allow scaling of low frequency signal sensors.

Pseudo-resistors may be implemented with p-type metal-oxide-semiconductor (PMOS) transistors. As shown e.g. in Benko et al, "*Bio-Amplifier based on MOS bipolar Pseudo-Resistors: A New Approach using its non-linear characteristic*", Journal of Integrated Circuits and Systems 2016, Vol. 11, No. 2, pages 132-139, the MOS transistors body is connected to the source and the gate is connected to the drain, such that the pseudo-resistor acts like a PMOS diode for positive gate-source voltage and like a bipolar diode for negative gate-source voltage. It is mentioned that for a back-to-back connection of pseudo-resistors, a linear trend in the current-voltage characteristic may be observed in an interval between ±100 mV.

However, the pseudo-resistors may be associated with leakage currents flowing through the PMOS transistors. Further, if the pseudo-resistors are exposed to light, excessive leakage currents may be generated. Leakage currents may severely affect performance and functionality of amplifiers.

SUMMARY

An objective of the present inventive concept is to provide a pseudo-resistor structure that enables at least a reduction of leakage currents occurring in a pseudo-resistor structure.

These and other objects of the present inventive concept are at least partly met by the invention as defined in the independent claims. Preferred embodiments are set out in the dependent claims.

According to a first aspect, there is provided a pseudo-resistor structure, comprising: a first p-type metal-oxide-semiconductor (PMOS) transistor or a first PN diode, a second PMOS transistor or a second PN diode, wherein each of the first PMOS transistor ($100a$) or the first PN diode and the second PMOS transistor ($100b$) or second PN diode is configured as a two-terminal device having a positive and a negative terminal, wherein the positive terminal of the first PMOS transistor ($100a$) or the first PN diode is connected to the positive terminal of the second PMOS transistor ($100b$) or the second PN diode and the negative terminal of the first PMOS transistor ($100a$) or the first PN diode is connected to an input of the pseudo-resistor structure and wherein the negative terminal of the second PMOS transistor or second PN diode is connected to an output of the pseudo-resistor structure, and a dummy transistor or dummy diode connected to the input of the pseudo-resistor structure, wherein the dummy transistor or dummy diode is further connected to a bias voltage for compensating a leakage current through the first and the second PMOS transistors or first and second PN diodes.

According to the first aspect, a pseudo-resistor structure is provided which is able to compensate leakage currents occurring in the pseudo-resistor structure, such that the leakage currents may cancel out. The pseudo-resistor structure may be especially suitable for use with small-scale technologies, in which transistor or diode structures are very close to each other and in which leakage currents may therefore be larger.

The pseudo-resistor structure of the first aspect is based on an insight that parasitic junction diodes in the pseudo-resistor structure. For instance, if transistors are used, parasitic junction diodes may be formed between a p-doped region associated with the drain and n-type well of the PMOS transistor and also between a p-type substrate on which the pseudo-resistor structure is formed and the n-type well of the PMOS transistor. Similarly, if PN diodes are used, parasitic junction diodes may be formed between a p-doped region associated with the positive terminal and a n-type well of the PN diode and also between a p-type substrate on which the pseudo-resistor structure is formed and the n-type well of the PN diode. These junction diodes may each cause a leakage current through the pseudo-resistor structure.

According to the first aspect, a first and a second PMOS transistor or a first and a second PN diode are provided. The positive terminals of the PMOS transistors or PN diodes may be connected to each other. The first and second PMOS transistors or PN diodes could thus be said to be connected in a back-to-back configuration. The back-to-back configuration implies that, for a pseudo-resistor structure comprising a first and a second PMOS transistor, corresponding leakage currents due to the parasitic junction diode between a p-doped region associated with the drain and n-type well of the PMOS transistor may occur in the first and the second PMOS transistors. Similarly, for a pseudo-resistor structure comprising a first and a second PN diode, corresponding leakage currents due to the parasitic junction diode between a p-doped region associated with the positive terminal and the n-type well of the PN diode may occur in the first and the second PN diodes. These leakage currents may be considered to cancel each other since the leakage currents are flowing in opposite directions over the same resistances (pseudo-resistors).

Further, it is an insight of the invention that a leakage current may remain based on the parasitic junction diode formed between the p-type substrate on which the pseudo-resistor structure is formed and the n-type well of the first PMOS transistor or PN diode. This leakage current may flow to the n-doped region associated with the negative terminal, which is connected to the input. Thus, according to the first aspect, the pseudo-resistor structure further comprises a dummy transistor or dummy diode which may compensate for the remaining leakage current in the back-to-back pseudo-resistors. The dummy transistor or dummy diode may be connected to a bias voltage in order to compensate the leakage current.

According to an embodiment, the first PMOS transistor or first PN diode is a first PMOS transistor, the second PMOS transistor or second PN diode is a second PMOS transistor and the dummy transistor or dummy diode is a dummy transistor, wherein a gate and a drain of the first PMOS transistor are connected to a gate and a drain of the second PMOS transistor and wherein a source and a bulk node of the first PMOS transistor are connected to the input of the pseudo-resistor structure and wherein a source and a bulk node of the second PMOS transistor are connected to the output of the pseudo-resistor structure.

Thus, according to this embodiment, the pseudo-resistor structure is based on PMOS transistors. The gate and the drain of each of the first PMOS transistor and the second PMOS transistor may be connected to each other to form a positive terminal. Further, the source and the bulk node of each of the first PMOS transistor and the second PMOS transistor may be connected to each other to form a negative terminal.

Further, the first and second PMOS transistors are connected in a back-to-back configuration, such that, as mentioned above, some leakage currents in the first and second PMOS transistors may be considered to cancel each other. Also, a dummy transistor may be provided in order to compensate for a remaining leakage current.

According to an embodiment, the dummy transistor comprises an n-type metal-oxide-semiconductor (NMOS) transistor formed in a deep n-type well.

The use of a NMOS transistor in a deep n-type well implies that a leakage current may be formed in the dummy transistor flowing between an internal p-well in the NMOS transistor and the deep n-type well. This leakage current may compensate leakage current in the back-to-back pseudo-resistors so as to cancel out the leakage current.

According to an embodiment, a drain, a source, a gate, and a bulk node of the NMOS transistor are connected to the source and the bulk node of the first PMOS transistor. This implies that terminals of the dummy transistor are connected to each other and to the input, so as to avoid any other leakage currents in the dummy transistor apart from the current that is to compensate leakage current in the back-to-back pseudo-resistors.

According to an embodiment, a terminal of the dummy transistor is connected to the deep n-type well and wherein the terminal is further connected to the bias voltage. This implies that the bias voltage is connected to the deep n-type well and that the bias voltage may thus control a leakage current in the dummy transistor flowing between an internal p-well in the NMOS transistor and the deep n-type well.

According to an embodiment, a p-n junction of the first PMOS transistor has a similar size to a p-n junction of the NMOS transistor. This implies that the parasitic junction diodes of the first PMOS transistor and of the dummy NMOS transistor have similar dimensions, facilitating that the leakage currents through the first PMOS transistor and through the dummy transistor cancel out each other.

According to an embodiment, the terminal is connected to a bias voltage such that the DC voltage between the terminal and the input of the pseudo-resistor structure is similar to a DC voltage between the input of the pseudo-resistor structure and ground. This implies that a DC voltage across the p-n junction of the first PMOS transistor is similar to a DC voltage across the p-n junction of the dummy NMOS transistor such that the leakage currents through the first PMOS transistor and through the dummy transistor cancel out each other.

According to an embodiment, the first PMOS transistor or first PN diode is a first PN diode, the second PMOS transistor or second PN diode is a second PN diode and the dummy transistor or dummy diode is a dummy diode, and wherein the dummy diode comprises an NP diode formed in a deep n-type well.

Thus, according to this embodiment, the pseudo-resistor structure is based on PN diodes. The first and second PN diodes are connected in a back-to-back configuration, such that, as mentioned above, some leakage currents in the first and second PN diodes may be considered to cancel each other. Also, a dummy diode may be provided in order to compensate for a remaining leakage current.

The use of a NP diode in a deep n-type well implies that a leakage current may be formed in the dummy diode flowing between an internal p-well in the NMOS transistor and the deep n-type well. This leakage current may compensate leakage current in the back-to-back pseudo-resistors so as to cancel out the leakage current.

According to an embodiment, a positive terminal and a negative terminal of the dummy diode are connected to the negative terminal of the first PN diode. This implies that terminals of the dummy diode are connected to each other and to the input, so as to avoid any other leakage currents in the dummy diode apart from the current that is to compensate leakage current in the back-to-back pseudo-resistors.

The pseudo-resistor structure according to claim 8 or 9, wherein a terminal of the dummy diode is connected to the deep n-type well and wherein the terminal of the dummy diode is further connected to the bias voltage. This implies that the bias voltage is connected to the deep n-type well and that the bias voltage may thus control a leakage current in the dummy diode flowing between an internal p-well in the NP diode and the deep n-type well.

According to a second aspect of the invention, there is provided a closed-loop operational amplifier circuit, said closed-loop amplifier circuit comprising: an operational amplifier, comprising a first and a second input node and an output node, a feedback structure, connected between the output node and the first input node, wherein the feedback structure comprises a pseudo-resistor structure according to the first aspect.

Effects and features of this second aspect are largely analogous to those described above in connection with the first aspect. Embodiments mentioned in relation to the first aspect are largely compatible with the second aspect.

The use of a pseudo-resistor structure is particularly advantageous in a closed-loop operational amplifier circuit. The closed-loop operational amplifier having the pseudo-resistor structure in the feedback structure may be configured to amplify alternating current (AC) information only, while the operational amplifier may behave as a buffer in DC.

Thanks to the pseudo-resistor structure being configured to enable at least a reduction of leakage currents, a desired performance and functionality of the operational amplifier circuit may be achieved.

According to an embodiment, the closed-loop operational amplifier circuit, further comprises: a second pseudo-resistor structure according to the first aspect, wherein the second pseudo-resistor structure is connected to the second input node and to a reference bias voltage.

The input nodes may not be properly DC biased, causing a DC offset. The use of the first and the second pseudo-resistor may ensure that the input nodes are biased to the reference bias DC voltage. If a leakage current would flow through the pseudo-resistor structures, a voltage offset may cause the DC voltage at the input nodes not to equal the reference bias voltage, which could affect the performance and functionality of the operational amplifier. Thanks to the pseudo-resistor structures being configured to enable at least a reduction of leakage currents, the risk of a voltage offset at the input nodes of the operational amplifier is reduced.

According to a third aspect, there is provided a bio-potential sensor, said sensor comprising: an electrode configured for sensing a bio-potential signal, a closed-loop operational amplifier circuit according to the second aspect, wherein the closed-loop operational amplifier circuit is connected to the electrode for amplifying a low frequency signal without amplifying a DC voltage.

Effects and features of this third aspect are largely analogous to those described above in connection with the first and second aspects. Embodiments mentioned in relation to the first and second aspects are largely compatible with the third aspect.

The closed-loop operational amplifier according to the second aspect is able to amplify a AC information only. Thus, low-level signals of a low frequency may be amplified and extracted, even in presence of large DC offsets. This may typically be needed in a bio-potential sensor having interfaces between electrodes and biological substance, such as tissue, wherein a large DC offset may typically occur across differential recording electrodes. Hence, the bio-potential sensor may advantageously make use of a closed-loop operational amplifier, which enables a desired performance and functionality of the operational amplifier circuit to be achieved.

The bio-potential sensor may be configured to sense any type of signal associated with a potential. Thus, the bio-potential sensor may be configured to e.g. sense an electrical characteristic of the biological substance, such as a bio-impedance. The bio-impedance could for instance be used as a measure of body composition, but may also provide other type of information, such as respiratory information based on modulation of a bio-impedance signal. According to an alternative, the bio-potential sensor may be configured to sense a bio-electric signal, which may be transmitted in the biological substance.

Depending on application, the bio-potential sensor may be differently configured for enabling obtaining a signal of interest. For instance, the bio-potential sensor may be configured to be arranged on a skin surface. The bio-potential sensor may then be configured to acquire a bio-impedance measurement, but may alternatively be configured to sense a bio-electric signal transmitted close to or in the skin surface.

The bio-potential sensor may according to other alternatives be implantable into a body or may be configured for in vitro sensing in cell cultures or the like.

Thanks to the pseudo-resistor structure having reduced leakage current, the pseudo-resistor structure may also be relatively insensitive to being exposed to light. This may be particularly useful in a bio-potential sensor, which may be combined with a further sensor using light-based measurements, e.g. based on a light source emitting light for enabling analysis based on reflected or transmitted light in the biological substance. Thus, any stray light which may originate from such a further sensor will not affect or will insignificantly affect a performance of the bio-potential sensor. This facilitates combining the bio-potential sensor with other type of sensors using light sources.

According to a fourth aspect, there is provided a biomedical device comprising a bio-potential sensor according to the third aspect.

Effects and features of this fourth aspect are largely analogous to those described above in connection with the first, second, and third aspects. Embodiments mentioned in relation to the first, second, and third aspects are largely compatible with the fourth aspect.

The biomedical device may use input from the bio-potential sensor for diagnostic and/or therapeutic purposes. For instance, the biomedical device may be used in diagnosis, prevention, monitoring, treatment or alleviation of a disease or a condition of a subject. The sensing of a bio-potential signal may be used as input for assessing a condition of a subject in order to allow drawing diagnostic conclusions or provide input to treatment of the subject.

BRIEF DESCRIPTION OF THE DRAWINGS

The above, as well as additional objects, features and advantages of the present inventive concept, will be better understood through the following illustrative and non-limiting detailed description, with reference to the appended drawings. In the drawings like reference numerals will be used for like elements unless stated otherwise.

FIG. 4 is a schematic view of a pseudo-resistor using a PN diode illustrating leakage currents in the pseudo-resistor.

FIG. 5 is a schematic view of two pseudo-resistors using PN diodes connected in a back-to-back configuration illustrating leakage currents in the two pseudo-resistors.

DETAILED DESCRIPTION

In applications where a low frequency signal is to be sensed, pseudo-resistors may be advantageously used to emulate very large resistances that form DC blocking high-pass filters. A pseudo-resistor may be formed based on a transistor structure or on a diode structure.

Figure 1:
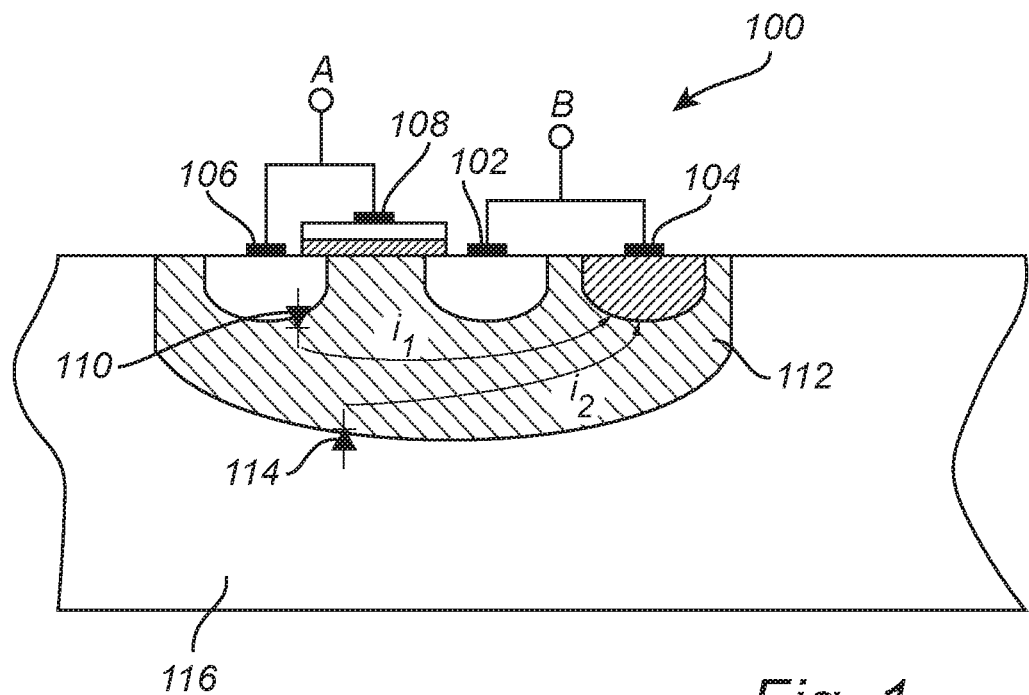
FIG. 1 is a schematic view of a pseudo-resistor using a PMOS transistor illustrating leakage currents in the pseudo-resistor.

As shown in FIG. 1, a pseudo-resistor 100 may be implemented as a PMOS transistor, in which a source connection 102 and a bulk connection 104 are connected to each other, and a drain connection 106 and a gate connection 108 are connected to each other. The pseudo-resistor 100 may thus form a two-terminal device. The pseudo-resistor 100 may provide a Tera-ohm resistance, which can be achieved in a very small area.

However, parasitic junction diodes may be formed in the PMOS transistor and may cause leakage currents flowing through the PMOS transistor. As illustrated in FIG. 1, a first parasitic junction diode 110 may be formed between a p-doped region associated with the drain 106 and an n-type well 112 of the PMOS transistor. Also, a second parasitic junction diode 114 may be formed between a p-type substrate 116 on which the pseudo-resistor 100 is formed and the n-type well 112 of the PMOS transistor. As illustrated in FIG. 1, the first parasitic junction diode 110 may give rise to a leakage current i1 towards an n-doped region associated with the bulk connection 104. The second parasitic junction diode 114 may give rise to a leakage current i2 towards the n-doped region associated with the bulk connection 104.

The leakage currents caused by the parasitic junction diodes 110, 114 may generate large DC offsets across the pseudo-resistor 100. The issue of DC offsets is becoming more severe for scaled technologies in which the leakage currents are much larger. Additionally, excessive leakage currents can also be generated if the pseudo-resistor 100 is exposed to light, which can especially occur in applications using bare-silicon dies. The leakage currents may severely affect the performance and functionality of circuits including the pseudo-resistor 100, for instance an amplifier for amplifying a low frequency signal.

Figure 2:
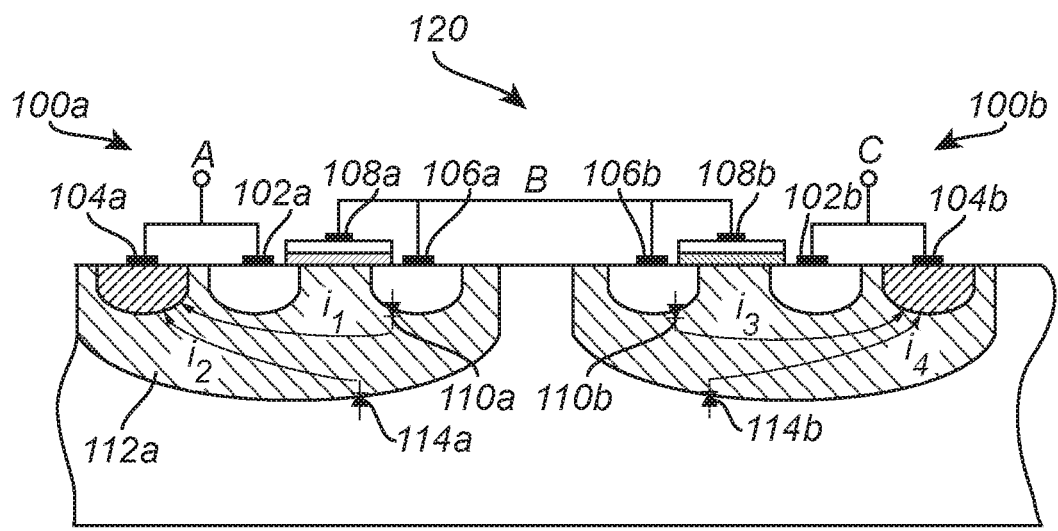
FIG. 2 is a schematic view of two pseudo-resistors using PMOS transistors connected in a back-to-back configuration illustrating leakage currents in the two pseudo-resistors.

In FIG. 2, a pseudo-resistor structure 120 is illustrated, wherein the pseudo-resistor structure 120 comprises a back-to-back configuration of a first PMOS transistor 100a and a second PMOS transistor 100b. For each of the first PMOS transistor 100a and the second PMOS transistor 100b, the source connection 102a, 102b and the bulk connection 104a, 104b are connected to each other, and the drain connection 106a, 106b and the gate connection 108a, 108b are connected to each other. Further, the gate 108a and the drain 106a of the first PMOS transistor 100a are connected to the gate 108b and the drain 106b of the second PMOS transistor 100b. Such a back-to-back configuration of the first and the second PMOS transistors 100a, 100b may be used to improve linearity of the pseudo-resistor structure 120.

The source 102a and the bulk node 104a of the first PMOS transistor 100a are connected to an input, illustrated by node A in FIG. 2, of the pseudo-resistor structure 120. Further, the source 102b and the bulk node 104b of the second PMOS transistor 100b are connected to an output, illustrated by node B in FIG. 2, of the pseudo-resistor structure 120.

The parasitic junction diodes 110a, 110b, 114a, 114b and leakage currents present $i_1$, $i_2$, $i_3$, $i_4$ in a back-to-back pseudo-resistor configuration are illustrated in FIG. 2.

Assuming that the node A will be connected to a high-impedance input node and the node C will be connected to a low-impedance output node, the leakage currents $i_1$ and $i_3$ may be considered to cancel each other, since the leakage currents are flowing in opposite directions over the same resistances (pseudo-resistors).

The leakage current $i_4$ of the second PMOS transistor 100b does not flow through the pseudo-resistors but to the output node C and, therefore, does not generate any unwanted DC offset across the pseudo-resistor structure 120.

However, since the input node A is a high-impedance node, the current $i_2$ in the first PMOS transistor 100a will flow through the two pseudo-resistors 100a, 100b causing a DC offset across the pseudo-resistor structure 120.

Figure 3:
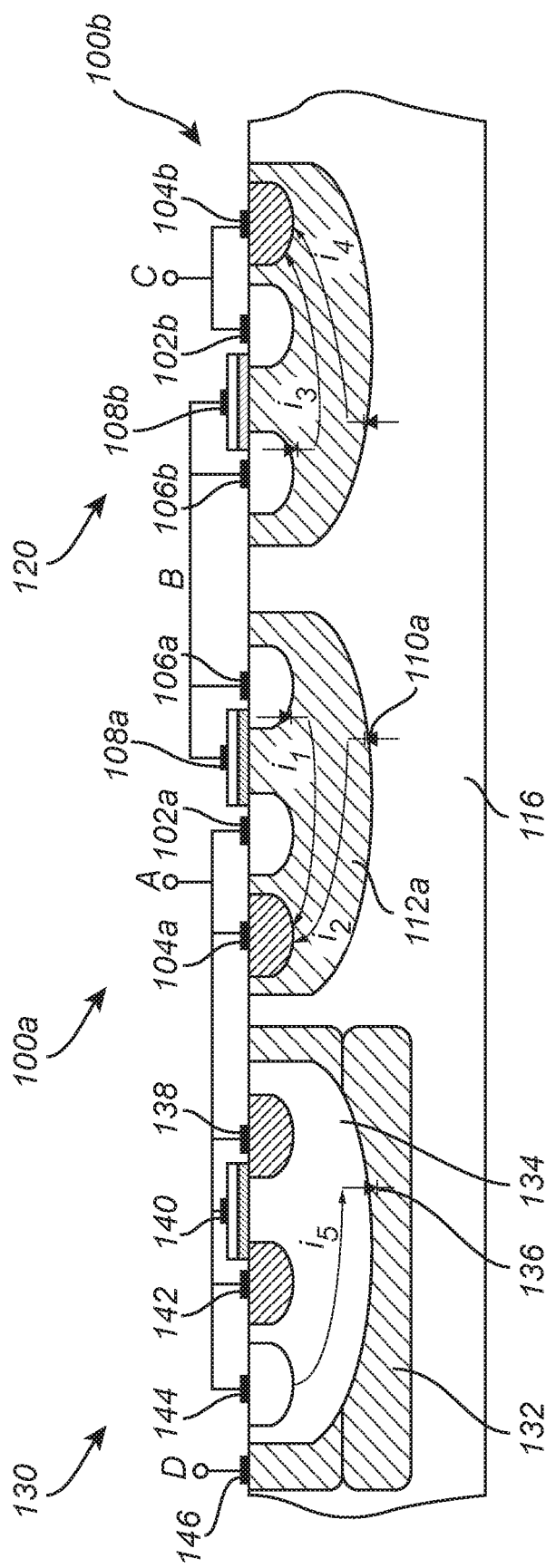
FIG. 3 is a schematic view of a pseudo-resistor structure according to a first embodiment.

As illustrated in FIG. 3, the pseudo-resistor structure 120 may further comprise a dummy transistor 130. The dummy transistor 130 may compensate the leakage current $i_2$ in the first PMOS transistor 100a.

The dummy transistor 130 may be configured so that a leakage current $i_5$ may be formed in the dummy transistor 130, wherein the leakage current $i_5$ in the dummy transistor 130 is as large as the remaining leakage current $i_2$ in the first PMOS transistor 100a so that the leakage currents $i_5$ and $i_2$ will cancel out each other.

The dummy transistor 130 may comprise a NMOS transistor formed in a deep n-type well 132 in the p-type substrate 116. Thus, a p-type well 134 is formed in the deep n-type well 132 and the NMOS transistor is formed on the p-type well 134. A parasitic junction diode 136 may be formed between the p-type well 134 and the deep n-type well 132.

A drain connection 138, a gate connection 140, a source connection 142 and a bulk node connection 144 of the dummy transistor 130 may all be connected to each other. This implies that there is no or insubstantial leakage currents to any parasitic junction diodes between the p-type well 134 and n-doped regions associated with the drain 138 and the source 142 of the dummy transistor 130.

Further, the drain 138, the gate 140, the source 142 and the bulk node 144 of the dummy transistor 130 may be connected to the source 102a and the bulk node 104a of the first PMOS transistor 100a and, hence, to the input node A. The dummy transistor 130 may further comprise a terminal 146, which is connected to the deep n-type well 132. The terminal 146 may be connected to a bias voltage, as indicated by node D in FIG. 3. The dummy transistor 130 may thus provide biasing conditions in relation to the node A, wherein the biasing conditions are similar to the biasing conditions in the first PMOS transistor 100a causing the remaining leakage current $i_2$.

The remaining leakage current $i_5$ in the dummy transistor 130, flowing between the internal p-type well 134 and the deep n-type well 132, may be configured to compensate the leakage current $i_2$.

The bias voltage connected to node D may control the leakage current $i_5$ so that the leakage currents $i_5$ and $i_2$ will cancel out each other. The compensation of the remaining leakage current $i_2$ may be facilitated if the parasitic junction diodes 110a and 136 have same dimensions, i.e. the p-n junctions in which the parasitic junction diodes 110a and 136 are formed have a similar or equal size.

The compensation of the remaining leakage current $i_2$ may be further facilitated if DC voltages across the junctions are the same, i.e. the DC voltage between nodes D and A and between node A and ground (i.e. the p-type substrate 116) are equal or similar.

The compensation of the remaining leakage current $i_2$ may be further facilitated if doping of the deep n-type well 132 and the n-type well 112a and doping of the p-type well 134 and the p-type substrate 116 are similar.

With the above conditions, the bias voltage to be connected to node D may be set to double the DC voltage provided at node A, such that the dummy transistor 130 may compensate the remaining leakage current $i_2$ in the back-to-back pseudo-resistors 100a, 100b.

Referring now to FIG. 4, a pseudo-resistor structure using PN diodes will be described. The pseudo-resistor structure has similarities to the pseudo-resistor structure 120 using PMOS transistors, so for brevity all the details of the pseudo-resistor structure using PN diodes may not be set out below. A skilled person would understand how the implementation using PN diodes may be made similar to the implementation using PMOS transistors based on the description below.

As shown in FIG. 4, a pseudo-resistor 150 may be implemented as a PN diode having a positive terminal 152 and a negative terminal 154. The pseudo-resistor 150 may thus form a two-terminal device.

Similar to a pseudo-resistor using PMOS transistors, parasitic junction diodes may be formed in the PN diode 150 and may cause leakage currents flowing through the PN diode 150. As illustrated in FIG. 4, a first parasitic junction diode 156 may be formed between a p-doped region associated with the positive terminal 152 and an n-type well 158 of the PN diode. Also, a second parasitic junction diode 160 may be formed between a p-type substrate 162 on which the pseudo-resistor 100 is formed and the n-type well 158 of the PN diode. As illustrated in FIG. 4, the first parasitic junction diode 156 may give rise to a leakage current $i_6$ towards an n-doped region associated with the negative terminal 154. The second parasitic junction diode 160 may give rise to a leakage current $i_7$ towards the n-doped region associated with the negative terminal 154.

In FIG. 5, a pseudo-resistor structure 170 is illustrated, wherein the pseudo-resistor structure 170 comprises a back-to-back configuration of a first PN diode 150a and a second PN diode 150b. The positive terminal 152a of the first PN diode 150a may be connected to the positive terminal 152b of the second PN diode 150b.

The negative terminal 154a of the first PN diode 150a is connected to an input, illustrated by node A in FIG. 5, of the pseudo-resistor structure 170. Further, the negative terminal 154b of the second PN diode 150b is connected to an output, illustrated by node B in FIG. 5, of the pseudo-resistor structure 170.

The parasitic junction diodes 156a, 156b, 160a, 160b and leakage currents present $i_6$, $i_7$, $i_8$, $i_9$ in a back-to-back pseudo-resistor configuration are illustrated in FIG. 5.

Similar to the set-up using PMOS transistors, the leakage current $i_7$ in the first PN diode 150a will flow through the two pseudo-resistors 150a, 150b causing a DC offset across the pseudo-resistor structure 170.

Figure 6:
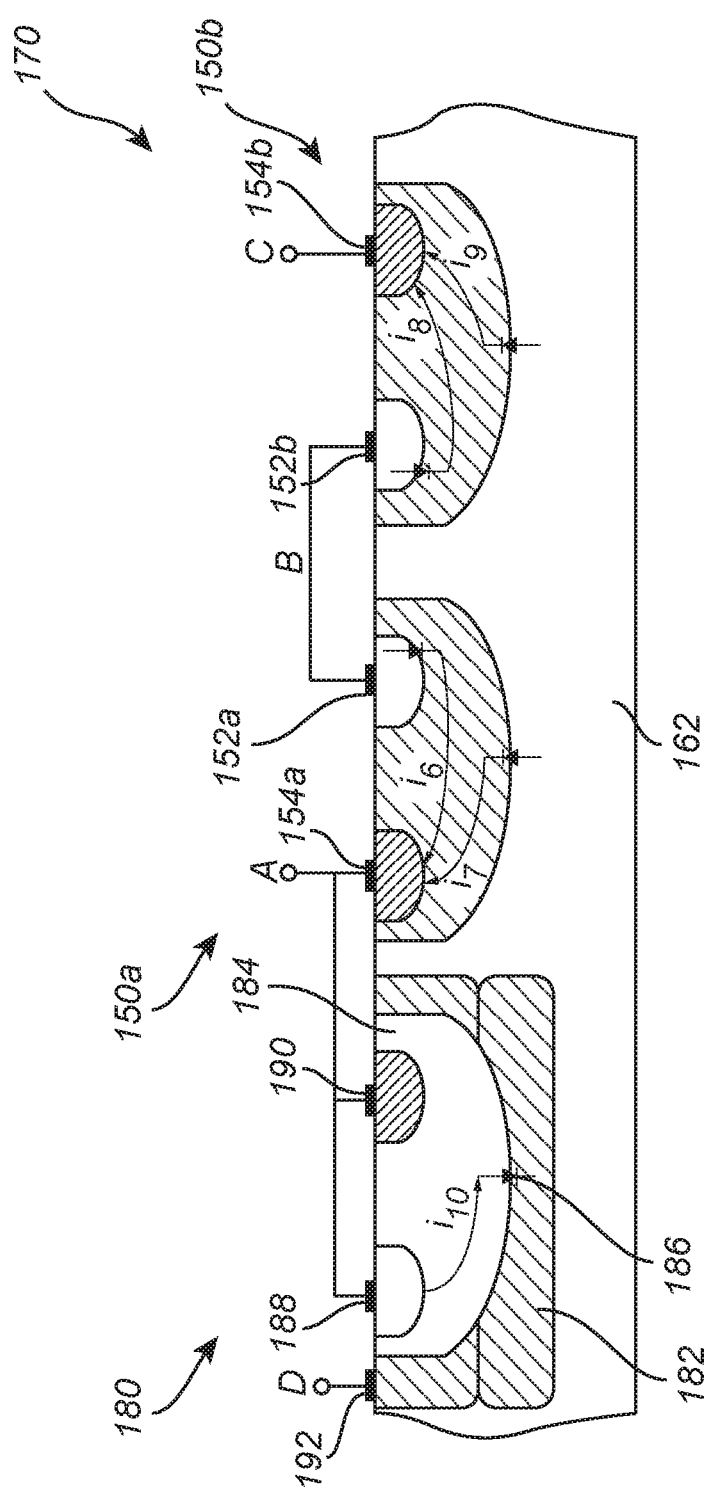
FIG. 6 is a schematic view of a pseudo-resistor structure according to a second embodiment.

As illustrated in FIG. 6, the pseudo-resistor structure 170 may further comprise a dummy diode 180. The dummy diode 180 may compensate the leakage current $i_7$ in the first PN diode 150a.

The dummy diode 180 may be configured so that a leakage current $i_{10}$ may be formed in the dummy diode 180, wherein the leakage current $i_{10}$ in the dummy diode 180 is as large as the remaining leakage current $i_7$ in the first PN diode 150a so that the leakage currents $i_{10}$ and $i_7$ will cancel out each other.

The dummy diode 180 may comprise an NP diode formed in a deep n-type well 182 in the p-type substrate 162. Thus, a p-type well 184 is formed in the deep n-type well 182 and the NP diode is formed on the p-type well 184. A parasitic junction diode 186 may be formed between the p-type well 184 and the deep n-type well 182.

A positive terminal 188 and a negative terminal 190 of the dummy diode 180 may be connected to each other. This implies that there is no or insubstantial leakage currents to any parasitic junction diodes between the p-type well 134 and n-doped regions associated with the negative terminal of the dummy diode 180.

Further, the positive terminal 188 and the negative terminal 190 of the dummy diode 180 may be connected to the negative terminal 154a of the first PN diode 150a and, hence, to the input node A. The dummy diode 180 may further comprise a terminal 192, which is connected to the deep n-type well 182. The terminal 192 may be connected to a bias voltage, as indicated by node D in FIG. 6. The dummy diode 180 may thus provide biasing conditions in relation to the node A, wherein the biasing conditions are similar to the biasing conditions in the first PN diode 150a causing the remaining leakage current $i_7$.

The remaining leakage current $i_{10}$ in the dummy diode 180, flowing between the internal p-type well 184 and the deep n-type well 182, may be configured to compensate the leakage current $i_7$.

The bias voltage connected to node D may control the leakage current $i_{10}$ so that the leakage currents $i_{10}$ and $i_7$ will cancel out each other. The compensation of the remaining leakage current $i_7$ may be facilitated if the parasitic junction diodes 156a and 186 have same dimensions, i.e. the p-n junctions in which the parasitic junction diodes 156a and 186 are formed have a similar or equal size.

The compensation of the remaining leakage current $i_7$ may be further facilitated if DC voltages across the junctions are the same, i.e. the DC voltage between nodes D and A and between node A and ground (i.e. the p-type substrate 162) are equal or similar.

The compensation of the remaining leakage current $i_7$ may be further facilitated if doping of the deep n-type well 182 and the n-type well 158a and doping of the p-type well 184 and the p-type substrate 162 are similar.

With the above conditions, the bias voltage to be connected to node D may be set to double the DC voltage provided at node A, such that the dummy diode 180 may compensate the remaining leakage current $i_7$ in the back-to-back pseudo-resistors 150a, 150b.

Figure 7:
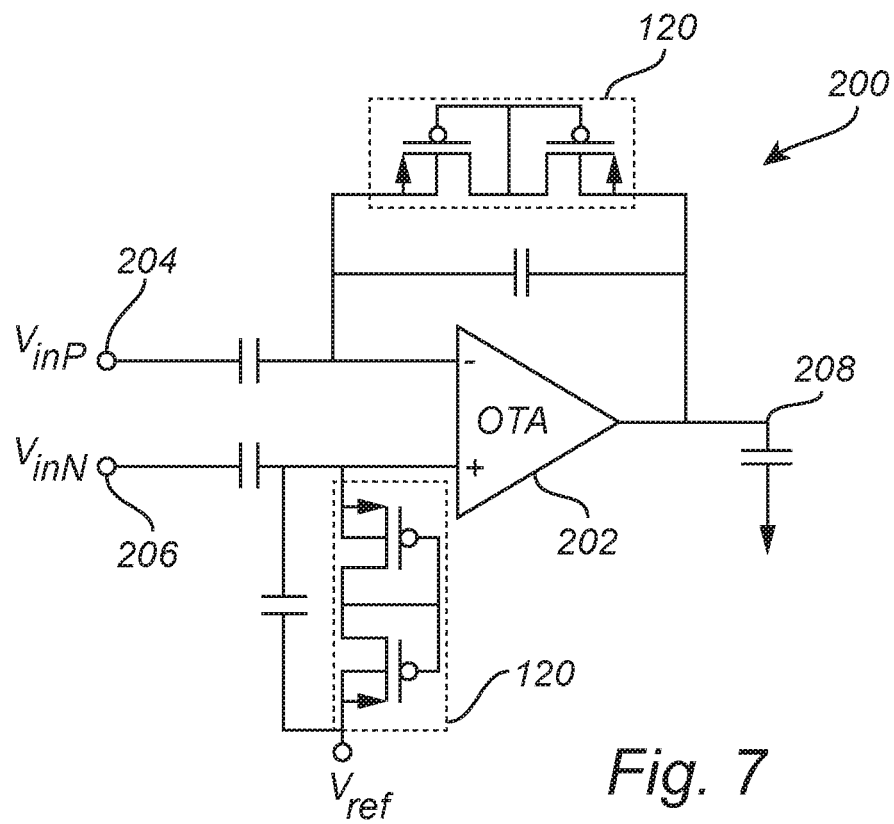
FIG. 7 is a schematic view of a closed-loop operational amplifier circuit according to an embodiment.

Referring now to FIG. 7, use of the pseudo-resistor structure 120 in a closed-loop operational amplifier circuit 200 will be discussed. Although, the discussion below is made with regard to using the pseudo-resistor structure 120 using PMOS transistors in the closed-loop operational amplifier circuit 200, it should be realized that the pseudo-resistor structure 170 using PN diodes may be used instead.

The pseudo-resistor structure 120 may be used in a capacitive-feedback closed-loop amplifier circuit 200 to bias input terminals 204, 206 of an operational amplifier 202 and to form a high-pass filter for very low frequency applications. The purpose of the filter is to reject the DC voltages.

An embodiment of a closed-loop operational amplifier circuit 200 is shown in FIG. 7. The closed-loop operational amplifier circuit 200 includes back-to-back pseudo-resistor structures 120. The back-to-back configuration is used for improving linearity of the pseudo-resistor structure 120 in the closed-loop operational amplifier circuit 200. Also, the back-to-back configuration facilitates reducing leakage currents through the pseudo-resistor structure 120.

The closed-loop operational amplifier circuit 200 in FIG. 7 comprises a CMOS operational transconductance amplifier (OTA) 202 in a capacitive-feedback inverting configuration. The two input nodes 204, 206 of the OTA 202 may be high-impedance nodes and no DC current flows through them. The output node 208 of the amplifier 202 may be a low impedance node.

The two input nodes 204, 206 may not be properly DC-biased in a capacitive-feedback configuration of the OTA 202 and for this reason pseudo-resistor structures 120 may be advantageously used. The two pseudo-resistor structures 120 in the closed-loop operational amplifier circuit 200 make sure that the input nodes 204, 206 of the OTA 202 are biased to a DC reference voltage applied to $V_{ref}$.

This amplifier configuration will amplify the AC information only, while it behaves as a buffer in DC, i.e. the DC reference voltage in $V_{ref}$ will be transferred to the two input nodes 204, 206 and then to the output node 208. The DC reference voltage $V_{ref}$ may typically be chosen as half of a supply voltage (i.e. $V_{DD}/2$) of an integrated circuit in which the closed-loop operational amplifier circuit 200 may be arranged.

If an excessive leakage current is flowing through the pseudo-resistors 120, the DC voltage at the input nodes 204, 206 will not be the same as the DC voltage of $V_{ref}$, due to the voltage offset caused by the leakage current. This may affect the functionality and performance of the amplifier circuit 200.

Hence, by using a pseudo-resistor structure 120 as described with reference to FIG. 3, leakage currents in the pseudo-resistor structures 120 of the closed-loop operational amplifier circuit 200 may be avoided and a desired performance and functionality of the closed-loop operational amplifier circuit 200 may be obtained.

In the embodiment of a closed-loop operational amplifier circuit 200 shown in FIG. 7, the DC voltage in $V_{ref}$, the output node 208 and the two input nodes 204, 206 may be half the supply voltage, i.e. $V_{DD}/2$. In such case, the leakage compensation in the pseudo-resistor structures 120 can be achieved if the node D is connected to $V_{DD}$.

Figure 8:
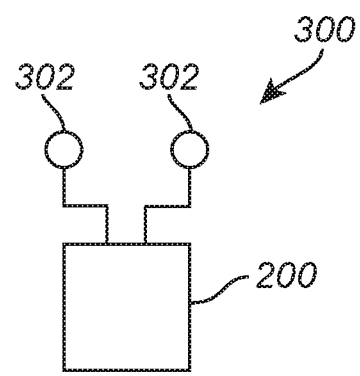
FIG. 8 is a schematic view of a bio-potential sensor according to an embodiment.

Referring now to FIG. 8, the closed-loop operational amplifier circuit 200 including pseudo-resistor structures 120 or 170 may be advantageously used in a bio-potential sensor 300. The closed-loop operational amplifier circuit 200 may provide amplification of AC information only. Thus, low-level signals of a low frequency may be amplified and extracted, even in presence of large DC offsets. This may typically be needed in a bio-potential sensor 300 having interfaces between electrodes and biological substance, such as tissue, wherein a large DC offset may typically occur across differential recording electrodes.

The bio-potential sensor 300 may comprise at least one electrode 302 for sensing a bio-potential signal. The bio-potential sensor 300 may comprise at least one electrode pair for sensing a bio-potential signal based on a potential difference between electrodes 302 in the electrode pair.

The bio-potential signal acquired by the at least one electrode 302 may be input to a closed-loop operational amplifier circuit 200 such that AC information in the bio-potential signal, which may be of very low frequency, may be amplified, even in presence of large DC offsets.

The amplified signal may then be transferred to further circuitry for processing and/or analyzing the amplified bio-potential signal.

The bio-potential sensor 300 may be configured to sense any type of signal associated with a potential. According to one embodiment, the bio-potential sensor 300 comprises a pair of electrodes 302 which are each adapted for being attached to a skin surface. This may be used in order to measure bio-impedance, e.g. by a current being passed between the electrodes 302 in the pair and a voltage between the electrodes 302 being measured in order to determine an impedance between the electrodes 302. A bio-impedance measurement may be used e.g. for determining a characteristic of the biological substance, such as a human body, through which the current is passed. The bio-impedance measurement may thus be used for determining a composition of the body, e.g. total body water.

However, the bio-impedance measurement may also be modulated, e.g. by respiratory action of a human on which measurements are performed. Thus, the bio-impedance measurement may also be used in order to extract information based on the modulation, such as respiratory rate.

According to another alternative, the bio-potential sensor 300 may be configured to sense an electrical signal transmitted to the biological substance. The bio-potential sensor 300 may thus comprise an electrode 302 which receives the electrical signal in order to measure it. The electrode 302 may be configured for being implanted into a body for sensing electrical signals transmitted in the body. Alternatively, measurements may be made in vitro, in which the electrode 302 may be arranged to sense electrical signals transmitted with in an in vitro sample, such as between or within cells.

Thus, it should be realized that a configuration of the bio-potential sensor 300 for acquiring a bio-potential signal may differ significantly. However, once the signal is acquired, the signal may advantageously be provided on inputs 204, 206 of a closed-loop operational amplifier circuit 200 as described with reference to FIG. 7, in order to amplify a low frequency signal even in presence of large DC offsets.

Thanks to the pseudo-resistor structure having reduced leakage current, the pseudo-resistor structure may also be relatively insensitive to being exposed to light. Thus, the bio-potential sensor 300 may be particularly suitable for being combined, e.g. integrated in a common housing or on a common chip, with a further sensor using light-based measurements. Such a further sensor may typically comprise a light source emitting light for enabling analysis based on interaction of the biological substance with emitted light. This implies that there may be a high risk of stray light from the light source, or after having interacted with the biological substance reaching the pseudo-resistor structures 120. Thanks to the pseudo-resistor structures 120 being configured to cancel out leakage currents, the stray light will not affect or will insignificantly affect a performance of the bio-potential sensor 300.

The bio-potential sensor 300 may be part of a biomedical device. The biomedical device may use bio-potential signals acquired by the bio-potential sensor 300 in order to make further analysis of the bio-potential signals. For instance, the biomedical device may comprise a processing unit, which may receive the bio-potential signals and may be configured to process the bio-potential signals in order to extract information of interest.

For instance, the biomedical device may be used in diagnosis, prevention, monitoring, treatment or alleviation of a disease or a condition of a subject. The sensing of a bio-potential signal may be used as input for assessing a condition of a subject in order to allow drawing diagnostic conclusions or provide input to treatment of the subject.

The biomedical device may thus comprise a processing unit, which is configured to receive bio-potential signals from a closed-loop operational amplifier circuit 200. The processing unit may be implemented in hardware or as any combination of software and hardware. For instance, the processing unit may be a central processing unit (CPU) comprising software for providing functionality of the biomedical device in a general-purpose processor. Alternatively, the processing unit may be implemented as firmware arranged e.g. in an embedded system. As a further alternative, the processing unit may be implemented as a special-purpose circuitry for providing specific logical operations. Thus, the processing unit may be provided in the form of an application-specific integrated circuit (ASIC), an application-specific instruction-set processor (ASIP) or a field-programmable gate array (FPGA).

In the above the inventive concept has mainly been described with reference to a limited number of examples. However, as is readily appreciated by a person skilled in the art, other examples than the ones disclosed above are equally possible within the scope of the inventive concept, as defined by the appended claims.

What is claimed is:

1. A pseudo-resistor structure, comprising:
a first p-type metal-oxide-semiconductor (PMOS) transistor;
a second PMOS transistor,
wherein each of the first PMOS transistor and the second PMOS transistor have a drain terminal, a gate terminal, a source terminal and a bulk terminal with the gate terminal shorted with the drain terminal and a positive terminal and the source terminal shorted with the bulk terminal and a negative terminal, wherein the positive terminal of the first PMOS transistor is connected to the positive terminal of the second PMOS transistor and the negative terminal of the first PMOS transistor is connected to an input of the pseudo-resistor structure and wherein the negative terminal of the second PMOS transistor is connected to an output of the pseudo-resistor structure; and
a dummy transistor connected to the input of the pseudo-resistor structure,
wherein the dummy transistor is further connected to a bias voltage,
wherein the dummy transistor is configured to compensate a leakage current through the first and the second PMOS transistors,
wherein the dummy transistor comprises an n-type metal-oxide-semiconductor, NMOS, transistor formed in a deep n-type well.

2. The pseudo-resistor structure according to claim 1, wherein a drain, a source, a gate, and a bulk node of the NMOS transistor are connected to the source and the bulk node of the first PMOS transistor.

3. The pseudo-resistor structure according to claim 1, wherein a terminal of the dummy transistor is connected to the deep n-type well and wherein the terminal is further connected to the bias voltage.

4. The pseudo-resistor structure according to claim 3, wherein the terminal is connected to the bias voltage such that a DC voltage between the terminal and the input of the pseudo-resistor structure is similar to a DC voltage between the input of the pseudo-resistor structure and ground.

5. The pseudo-resistor structure according to claim 1, wherein a p-n junction of the first PMOS transistor has a similar size to a p-n junction of the NMOS transistor.

6. A closed-loop operational amplifier circuit, said closed-loop operational amplifier circuit comprising:
an operational amplifier, comprising a first and a second input node and an output node; and
a feedback structure, connected between the output node and the first input node, wherein the feedback structure comprises a pseudo-resistor structure according to claim 1.

7. The closed-loop operational amplifier circuit according to claim 6, further comprising:
a second pseudo-resistor structure comprising
a first p-type metal-oxide-semiconductor (PMOS) transistor,
a second PMOS transistor or a second PN diode,
wherein each of the first PMOS transistor and the second PMOS transistor have a drain terminal, a gate terminal, a source terminal and a bulk terminal with the gate terminal shorted with the drain terminal and a positive terminal and the source terminal shorted with the bulk terminal and a negative terminal, wherein the positive terminal of the first PMOS transistor is connected to the positive terminal of the second PMOS transistor and the negative terminal of the first PMOS transistor is connected to an input of the second pseudo-resistor structure and wherein the negative terminal of the second PMOS transistor is connected to an output of the second pseudo-resistor structure, and
a dummy transistor connected to the input of the second pseudo-resistor structure, wherein the dummy transistor is further connected to a bias voltage, wherein the dummy transistor is configured to compensate a leakage current through the first and the second PMOS transistors,
wherein the second pseudo-resistor structure is connected to the second input node and to a reference bias voltage.

8. A bio-potential sensor, said sensor comprising:
an electrode configured for sensing a bio-potential signal; and
a closed-loop operational amplifier circuit according to claim 6, wherein the closed-loop operational amplifier circuit is connected to the electrode for amplifying a low frequency signal without amplifying a DC voltage.

9. A biomedical device comprising a bio-potential sensor according to claim 8.

10. A pseudo-resistor structure comprising:
a first PN diode;
a second PN diode,
wherein each of the first PN diode and the second PN diode have a positive terminal and a negative terminal, wherein the positive terminal of the first PN diode is connected to the positive terminal of the second PN diode and the negative terminal of the first PN diode is connected to an input of the pseudo-resistor structure and wherein the negative terminal of the second PN diode is connected to an output of the pseudo-resistor structure; and
a dummy diode connected to the input of the pseudo-resistor structure,
wherein the dummy diode is further connected to a bias voltage,
wherein the dummy diode is configured to compensate a leakage current through the first and second PN diodes.

11. The pseudo-resistor structure according to claim 10, wherein the dummy diode comprises an NP diode formed in a deep n-type well.

12. The pseudo-resistor structure according to claim 11, wherein a positive terminal and a negative terminal of the dummy diode are connected to the negative terminal of the first PN diode.

13. The pseudo-resistor structure according to claim 11, wherein a terminal of the dummy diode is connected to the deep n-type well and wherein the terminal of the dummy diode is further connected to the bias voltage.

14. A closed-loop operational amplifier circuit, said closed-loop operational amplifier circuit comprising:
an operational amplifier, comprising a first and a second input node and an output node, a feedback structure, connected between the output node and the first input node, wherein the feedback structure comprises a pseudo-resistor structure according to claim 10.

15. The closed-loop operational amplifier circuit according to claim 14, further comprising:
a second pseudo-resistor structure comprising
a first PN diode,
a second PN diode,
wherein each of the first PN diode and the second PN diode have a positive terminal and a negative terminal, wherein the positive terminal of the first PN diode is connected to the positive terminal of the second PN diode and the negative terminal of the first PN diode is connected to an input of the pseudo-resistor structure and wherein the negative terminal of the second PN diode is connected to an output of the pseudo-resistor structure, and
a dummy diode connected to the input of the pseudo-resistor structure,
wherein the dummy diode is further connected to a bias voltage, and wherein the dummy diode is configured to compensate a leakage current through the first and second PN diodes,
wherein the second pseudo-resistor structure is connected to the second input node and to a reference bias voltage.

16. A bio-potential sensor, said sensor comprising:
an electrode configured for sensing a bio-potential signal; and
a closed-loop operational amplifier circuit according to claim 14, wherein the closed-loop operational amplifier circuit is connected to the electrode for amplifying a low frequency signal without amplifying a DC voltage.

17. A biomedical device comprising a bio-potential sensor according to claim 16.

* * * * *